United States Patent
Wei

(10) Patent No.: US 9,675,645 B2
(45) Date of Patent: Jun. 13, 2017

(54) METHOD OF PREPARING BONE MATERIAL HAVING ENHANCED OSTEOINDUCTIVITY

(71) Applicant: Warsaw Orthopedic, Inc., Warsaw, IN (US)

(72) Inventor: Guobao Wei, Milltown, NJ (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 52 days.

(21) Appl. No.: 13/747,075

(22) Filed: Jan. 22, 2013

(65) Prior Publication Data

US 2014/0205674 A1    Jul. 24, 2014

(51) Int. Cl.
| | |
|---|---|
| A61K 35/32 | (2015.01) |
| A61K 9/14 | (2006.01) |
| A61K 9/70 | (2006.01) |
| A61F 13/00 | (2006.01) |
| C12N 5/00 | (2006.01) |
| A61K 38/18 | (2006.01) |
| A61K 38/39 | (2006.01) |
| A61K 35/14 | (2015.01) |
| A61K 35/28 | (2015.01) |
| A61L 27/36 | (2006.01) |

(52) U.S. Cl.
CPC .............. *A61K 35/32* (2013.01); *A61K 35/14* (2013.01); *A61K 35/28* (2013.01); *A61K 38/18* (2013.01); *A61K 38/1875* (2013.01); *A61K 38/39* (2013.01); *A61L 27/3608* (2013.01); *A61L 27/3683* (2013.01); *A61L 27/3691* (2013.01); *A61L 2430/06* (2013.01)

(58) Field of Classification Search
None
See application file for complete search history.

(56) References Cited

U.S. PATENT DOCUMENTS

| | | | |
|---|---|---|---|
| 2,742,488 A * | 4/1956 | Dufault | 554/22 |
| 3,476,855 A * | 11/1969 | Balassa | 424/548 |
| 5,846,484 A | 12/1998 | Scarborough et al. | |
| 2009/0087471 A1 * | 4/2009 | Shimp et al. | 424/423 |
| 2009/0130173 A1 * | 5/2009 | Behnam et al. | 424/426 |
| 2009/0220605 A1 | 9/2009 | Wei et al. | |
| 2010/0111906 A1 | 5/2010 | Scarborough et al. | |
| 2011/0070312 A1 * | 3/2011 | Wei et al. | 424/549 |
| 2011/0108644 A1 | 5/2011 | Morris et al. | |

FOREIGN PATENT DOCUMENTS

WO    WO2005065396 A    *    7/2005

OTHER PUBLICATIONS

White et al. (2006) J. Biotech. 123: pp. 504-515.*
Sachlos et al. (2008) Acta Biomaterialis 4: 1322-1331.*
Gruskin et al. (2012) Adv. Drug Delivery Rev. 64: 1063-1077.*
Gamradt et al. (2003) Clinical Orthopaedics and Related Research, No. 417, pp. 183-194.*
Mont et al. (2003) Clinical Orthopaedics and Related Research, No. 417, pp. 84-92.*

* cited by examiner

*Primary Examiner* — Chris R Tate
*Assistant Examiner* — Russell Fiebig
(74) *Attorney, Agent, or Firm* — Sorell Lenna & Schmidt LLP

(57) ABSTRACT

Methods for increasing osteoinductivity and/or surface area of bone material are provided. The methods include providing bone material and dehydrating the bone material with a solvent at its critical point. A useful solvent for critical point dehydrating is carbon dioxide. Critical point dehydration resulting in increased osteoinductivity and/or surface area can be applied to many types of bone material including bone particles, bone chips, bone fibers, bone matrices, both demineralized and non-demineralized. An implantable composition having an enhanced osteoinductivity and/or osteoconductivity is also provided. The implantable composition contains demineralized bone matrix dried at critical point of carbon dioxide. Critical point dried fibers of a demineralized bone matrix have a BET value from about 40 $m^2$/gm to about 100 $m^2$/gm, a value that is 100 times higher than corresponding vacuum dried or lyophilized DBM fibers.

13 Claims, No Drawings

METHOD OF PREPARING BONE MATERIAL HAVING ENHANCED OSTEOINDUCTIVITY

BACKGROUND

The rapid and effective repair of bone defects caused by injury, disease, wounds, or surgery is a goal of orthopedic surgery. Toward this end, a number of compositions and materials have been used or proposed for use in the repair of bone defects. The biological, physical, and mechanical properties of the compositions and materials are among the major factors influencing their suitability and performance in various orthopedic applications.

Autologous cancellous bone ("ACB"), also known as autograft or autogenous bone, is considered the gold standard for bone grafts. ACB is osteoinductive and nonimmunogenic, and, by definition, has all of the appropriate structural and functional characteristics appropriate for the particular recipient. Unfortunately, ACB is only available in a limited number of circumstances. Some individuals lack ACB of appropriate dimensions and quality for transplantation, and donor site pain and morbidity can pose serious problems for patients and their physicians.

Much effort has been invested in the identification or development of alternative bone graft materials. Demineralized bone matrix ("DBM") implants have been reported to be particularly useful. Demineralized bone matrix is typically derived from cadavers. The bone is removed aseptically and/or treated to kill any infectious agents. The bone is then particulated by milling or grinding and then the mineral components are extracted for example, by soaking the bone in an acidic solution.

DBM is a desirable component of bone graft materials because it provides an osteoinductive matrix and exhibits osteoconductive potential, thereby promoting bone growth and healings. DBM is osteoinductive due to the presence of active bone growth factors including bone morphogenic proteins (BMP). Osteoinductivity depends not only on the concentration of growth factors in DBM, but also on their availability to cells after implantation. Moreover, DBM is fully resorbable, and bone graft materials containing organic DBM are highly biocompatible because it contains many of the components of natural bone. Following implantation, the presence of DBM induces cellular recruitment to the site of injury. The recruited cells may eventually differentiate into bone forming cells. Such recruitment of cells leads to an increase in the rate of wound healing and, therefore, to faster recovery for the patient. Advantageously, DBM costs less than many other available organic bone composition additives, such as isolated BMPs.

Current DBM formulations have various drawbacks. First, while the collagen-based matrix of DBM is relatively stable, the active factors within the DBM matrix are rapidly degraded. The osteogenic activity of the DBM may be significantly degraded within 24 hours after implantation, and in some instances the osteogenic activity may be inactivated within 6 hours. Therefore, the factors associated with the DBM are only available to recruit cells to the site of injury for a short time after transplantation. For much of the healing process, which may take weeks to months, the implanted material may provide little or no assistance in recruiting cells.

Lyophilization is commonly used to reduce the moisture level of most bone material, including most DBM formulations and allograft implants. During lyophilization process, the surface of bone material is damaged leading to bone material having small surface area having decreased ability to absorb proteins, to anchor dependent cells such as osteoblasts, pre-osteoblasts and mesenchymal stem cells, and to retain growth factors, decreased, resulting in decreased osteoinductivity.

It is, therefore, desirable to provide methods of preparing bone material having increased surface area, increased biological activities including but not limited to osteoinductive activity. Further, it is also desirable to provide bone implants prepared from bone material having enhanced osteoinductivity and enhanced ability to grow and integrate into a host bone.

SUMMARY OF THE INVENTION

Methods for increasing osteoinductivity and/or surface area of bone material are provided. The methods include providing bone material and dehydrating the bone material with a solvent at its critical point. Useful solvents for critical point dehydrating comprise carbon dioxide or Freon. Critical point drying (CPD) of bone material comprises dehydrating the bone material at about 31.5° C. and about 1200 psi.

Methods described herein comprise providing bone material including without limitation both mineralized or demineralized bone fibers, bone chips, bone particles, bone matrices or mixtures thereof.

In various embodiments, the methods of this application further comprise providing a delivery vehicle and adding the dehydrated bone material to this delivery vehicle. The delivery vehicle can be a carrier or a covering.

In certain embodiments, the bone material provided in the methods described herein comprises a demineralized bone matrix which comprises demineralized bone fibers entangle in a carrier. The demineralized bone matrix can further include bone chips, bone particles of mixtures thereof.

In other embodiments, the methods described herein contemplate further adding an osteoinductive additive comprising bone marrow aspirant, blood, blood products, synthetic and naturally-derived bone morphogenic proteins, growth factors, particulate demineralized bone matrix, or mixtures thereof. In other embodiments, the methods described herein contemplate further adding an osteoconductive additive, the osteoconductive additive comprising calcium phosphates, collagen, collagen-derivatives, calcium sulfate, particulate demineralized bone matrix, naturally-derived allogenic bone mineral, naturally-derived autogenic bone mineral or mixtures thereof.

In various embodiments, CPD bone material comprises a surface area increased from about 3 to about 4 times when compared to surface area of untreated bone material. In other embodiments, CPD demineralized bone matrix comprises demineralized fibers having a surface area increased from about 6 to about 7 times when compared to surface area of bone fibers of untreated demineralized bone matrix.

In certain embodiments, CPD treated fibers of demineralized bone matrix comprise a surface area increased by about 100 times when compared to demineralized bone matrix fibers dried by vacuum or lyophilized.

In accordance with methods described herein, CPD dehydrated bone material comprises a surface area having a BET value from about 1 $m^2$/gm to about 5 $m^2$/gm. In other embodiments, CPD dehydrated bone fibers of a demineralized bone matrix comprise a surface area having a BET value from about 40 $m^2$/gm to about 100 $m^2$/gm.

In various embodiments, methods are provided for increasing surface area of bone material, these methods comprising providing a bone material; and dehydrating the bone material with a solvent at its critical point. In certain embodiments, critical point drying comprises dehydration with carbon dioxide at about 31.5° C. and about 1200 psi.

The present application also provides an implantable composition having an enhanced osteoinductivity, surface area and/or osteoconductivity, the composition comprising demineralized bone material dried at the critical point of carbon dioxide. CPD dehydrated demineralized bone fibers comprise a surface area having a BET value from about 1 to about 5 $m^2/gm$. In other embodiments, CPD demineralized bone matrix fibers comprise a surface area having a BET value from about 40 $m^2/gm$ to about 100 $m^2/gm$, or about 100 times more than lyophilized DBM fibers.

While multiple embodiments are disclosed, still other embodiments of the present disclosure will become apparent to those skilled in the art from the following detailed description, which shows and describes illustrative embodiments of the disclosure. As will be realized, the various embodiments of the present disclosure are capable of modifications in various obvious aspects, all without departing from the spirit and scope of the present disclosure. Accordingly, the detailed description is to be regarded as illustrative in nature and not restrictive.

DETAILED DESCRIPTION OF THE INVENTION

Definitions

For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about." Similarly, when values are expressed as approximations, by use of the antecedent "about," it will be understood that the particular value forms another embodiment that is +/−10% of the recited value. Accordingly, unless indicated to the contrary, the numerical parameters set forth in the following specification and attached claims are approximations that may vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques. Also, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value.

Notwithstanding that the numerical ranges and parameters setting forth the broad scope of this application are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, e.g., 5.5 to 10.

Bioactive agent or bioactive compound is used herein to refer to a compound or entity that alters, inhibits, activates, or otherwise affects biological or chemical events. For example, bioactive agents may include, but are not limited to, osteogenic or chondrogenic proteins or peptides, anti-AIDS substances, anti-cancer substances, antibiotics, immunosuppressants, anti-viral substances, enzyme inhibitors, hormones, neurotoxins, opioids, hypnotics, anti-histamines, lubricants, tranquilizers, anti-convulsants, muscle relaxants and anti-Parkinson substances, anti-spasmodics and muscle contractants including channel blockers, miotics and anti-cholinergics, anti-glaucoma compounds, anti-parasite and/or anti-protozoal compounds, modulators of cell-extracellular matrix interactions including cell growth inhibitors and antiadhesion molecules, vasodilating agents, inhibitors of DNA, RNA or protein synthesis, anti-hypertensives, analgesics, anti-pyretics, steroidal and non-steroidal anti-inflammatory agents, anti-angiogenic factors, angiogenic factors, anti-secretory factors, anticoagulants and/or antithrombotic agents, local anesthetics, ophthalmics, prostaglandins, anti-depressants, anti-psychotic substances, anti-emetics, and imaging agents. In certain embodiments, the bioactive agent is a drug. Bioactive agents further include RNAs, such as siRNA, and osteoclast stimulating factors. In some embodiments, the bioactive agent may be a factor that stops, removes, or reduces the activity of bone growth inhibitors. In some embodiments, the bioactive agent is a growth factor, cytokine, extracellular matrix molecule or a fragment or derivative thereof, for example, a cell attachment sequence such as RGD. A more complete listing of bioactive agents and specific drugs suitable for use in the present application may be found in "Pharmaceutical Substances: Syntheses, Patents, Applications" by Axel Kleemann and Jurgen Engel, Thieme Medical Publishing, 1999; the "Merck Index: An Encyclopedia of Chemicals, Drugs, and Biologicals", edited by Susan Budavari et al., CRC Press, 1996; and the United States Pharmacopeia-25/National Formulary-20, published by the United States Pharmacopeia Convention, Inc., Rockville Md., 2001, each of which is incorporated herein by reference.

Biocompatible, as used herein, is intended to describe materials that, upon administration in vivo, do not induce undesirable long-term effects.

Bone, as used herein, refers to bone that is cortical, cancellous or cortico-cancellous of autogenous, allogenic, xenogenic, or transgenic origin.

Demineralized, as used herein, refers to any material generated by removing mineral material from tissue, for example, bone tissue. In certain embodiments, the demineralized compositions described herein include preparations containing less than 5% calcium. In some embodiments, the demineralized compositions may comprise less than 1% calcium by weight. Partially demineralized bone is intended to refer to preparations with greater than 5% calcium by weight but containing less than 100% of the original starting amount of calcium. In some embodiments, demineralized bone has less than 95% of its original mineral content. "Demineralized" is intended to encompass such expressions as "substantially demineralized," "partially demineralized," "surface demineralized," and "fully demineralized." "Partially demineralized" is intended to encompass "surface demineralized."

Demineralized bone activity refers to the osteoinductive activity of demineralized bone.

Demineralized bone matrix (DBM), as used herein, refers to any material generated by removing mineral material from bone tissue. In some embodiments, the DBM compositions as used herein include preparations containing less than 5% calcium and, in some embodiments, less than 1% calcium by weight. In other embodiments, the DBM compositions comprise partially demineralized bone (e.g., preparations with greater than 5% calcium by weight but containing less than 100% of the original starting amount of calcium).

Osteoconductive, as used herein, refers to the ability of a substance to serve as a template or substance along which bone may grow.

Osteogenic, as used herein, refers to materials containing living cells capable of differentiation into bone tissue.

Osteoimplant, as used herein, refers to any implant prepared in accordance with the embodiments described herein and therefore may include expressions such as bone material, bone membrane, bone graft.

Osteoinductive, as used herein, refers to the quality of being able to recruit cells from the host that have the potential to stimulate new bone formation. Any material that can induce the formation of ectopic bone in the soft tissue of an animal is considered osteoinductive. For example, most osteoinductive materials induce bone formation in athymic rats when assayed according to the method of Edwards et al., "Osteoinduction of Human Demineralized Bone: Characterization in a Rat Model," Clinical Orthopaedics & Rel. Res., 357:219-228, December 1998, incorporated herein by reference.

In other instances, osteoinduction is considered to occur through cellular recruitment and induction of the recruited cells to an osteogenic phenotype. Osteoinductivity score refers to a score ranging from 0 to 4 as determined according to the method of Edwards et al. (1998) or an equivalent calibrated test. In the method of Edwards et al., a score of "0" represents no new bone formation; "1" represents 1%-25% of implant involved in new bone formation; "2" represents 26-50% of implant involved in new bone formation; "3" represents 51%-75% of implant involved in new bone formation; and "4" represents >75% of implant involved in new bone formation. In most instances, the score is assessed 28 days after implantation. However, the osteoinductivity score may be obtained at earlier time points such as 7, 14, or 21 days following implantation. In these instances it may be desirable to include a normal DBM control such as DBM powder without a carrier, and if possible, a positive control such as BMP. Occasionally osteoinductivity may also be scored at later time points such as 40, 60, or even 100 days following implantation. Percentage of osteoinductivity refers to an osteoinductivity score at a given time point expressed as a percentage of activity, of a specified reference score. Osteoinductivity may be assessed in an athymic rat or in a human. Generally, as discussed herein, an osteoinductive score is assessed based on osteoinductivity in an athymic rat.

Superficially demineralized, as used herein, refers to bone-derived elements possessing at least about 90 weight percent of their original inorganic mineral content, the expression "partially demineralized" as used herein refers to bone-derived elements possessing from about 8 to about 90 weight percent of their original inorganic mineral content and the expression "fully demineralized" as used herein refers to bone containing less than 8% of its original mineral context.

The expression "average length to average thickness ratio" as applied to the DBM fibers of the present application means the ratio of the longest average dimension of the fiber (average length) to its shortest average dimension (average thickness). This is also referred to as the "aspect ratio" of the fiber.

Fibrous, as used herein, refers to bone elements whose average length to average thickness ratio or aspect ratio of the fiber is from about 50:1 to about 1000:1. In overall appearance the fibrous bone elements can be described as bone fibers, threads, narrow strips, or thin sheets. Often, where thin sheets are produced, their edges tend to curl up toward each other. The fibrous bone elements can be substantially linear in appearance or they can be coiled to resemble springs. In some embodiments, the bone fibers are of irregular shapes including, for example, linear, serpentine or curved shapes. The bone fibers are preferably demineralized however some of the original mineral content may be retained when desirable for a particular embodiment.

Non-fibrous, as used herein, refers to elements that have an average width substantially larger than the average thickness of the fibrous bone element or aspect ratio of less than from about 50:1 to about 1000:1. Preferably the non-fibrous bone elements are shaped in a substantially regular manner or specific configuration, for example, triangular prism, sphere, cube, cylinder and other regular shapes. By contrast, particles such as chips, shards, or powders possess irregular or random geometries. It should be understood that some variation in dimension will occur in the production of the elements of this application and elements demonstrating such variability in dimension are within the scope of this application and are intended to be understood herein as being within the boundaries established by the expressions "mostly irregular" and "mostly regular".

Providing Bone Material

To prepare bone for implantation, the bone material is typically treated to clean, defat, sterilize, virally inactivate, disinfect, demineralize, dehydrate, and/or dry the bone matrix. Reference is made to U.S. Pat. No. 5,846,484, herein incorporated by reference in its entirety, for a description of example treatment of bone material intended for implantation.

The prior art provides treatment processes which, while beneficial for some purposes, generally work against conserving or retaining properties of bone. For example, removal of excess moisture from bone material reduces its antigenicity and is done to store and maintain the bone material in active condition for implantation. According to the American Association of Tissue Banks, whole bone containing no more than 6% moisture can be stored at ambient temperatures for up to five years after processing. Typical processes for drying bone include, for example, lyophilization or solvent drying. Typical processes for drying bone such as these, however, generally result in loss of the surface area of the bone. More specifically, during phase change of the moisture, surface tension of the bone is disturbed. This leads to denaturing of the collagen on the surface of the bone. As a result, dried bone typically exhibits a smooth surface comprising a smear surface of, among other things, denatured collagen fibrils. The collagen fibrils are generally no longer intact and do not retain secondary and tertiary surfaces. Accordingly, the collagen fibrils on the surface of the bone may be considered compromised. The smooth denatured surface does not exhibit the cell attractive qualities as the original textured surface of bone resulting in diminished ability to absorb and retain growth factors and other bioactive agents required for bone growth.

With specific reference to lyophilization, this process (freeze-drying, i.e., freezing, then sublimation of moisture) is commonly performed on bone to permit its shelf storage for up to several years without spoilage. Lyophilization typically involves freezing whole bone to temperatures as low as −70° C. prior to its packaging and storage. While lyophilization is thought to not disrupt physical properties of bone, it does adversely affect biomechanical properties of the bone by decreasing on the surface of the bone. Lyophilization can result in damage to the bone material due to dimensional changes that occur during the freezing and dehydrating operations.

Loss of surface area of the bone material may impact the growth factor retention, remodeling, cell attachment, and osteoinductivity of the bone material. Increasing the functional surface area of the bone material provides increased surface area to which proteins may adsorb and cells may attach. Anchorage-dependent cells are cells requiring a solid substratum for growth.

In some embodiments, biological activities of the bone matrix may be increased. Accordingly, the bone matrix, and compositions formed from the bone matrix, may variously be referred to as biologically active and/or, in some cases, osteoinductive. The biological activities of the bone composition provided herein that may be increased include but are not limited to osteoinductive activity, osteogenic activity, chondrogenic activity, wound healing activity, neurogenic activity, contraction-inducing activity, mitosis-inducing activity, differentiation-inducing activity, chemotactic activity, angiogenic or vasculogenic activity, exocytosis or endocytosis-inducing activity, or other cell or biological activity. It will be appreciated that bone formation processes frequently include a first stage of cartilage formation that creates the basic shape of the bone, which then becomes mineralized (endochondral bone formation). Thus, in many instances, chondrogenesis may be considered an early stage of osteogenesis, though of course it may also occur in other contexts.

Providing Bone Particles

The bone may be particulated. If the bone is demineralized, the bone may be particulated before, during or after demineralization. As previously discussed, in some embodiments, the bone may be monolithic and may not be particulated. Accordingly, while specific discussion is given to particulating bone, the methods disclosed herein and the nanoscale textured surfaces disclosed herein may be used with monolithic bones or implants, including, for example, surface demineralized implants or fully demineralized cortical bone implants.

The bone may be milled and ground or otherwise processed into particles of an appropriate size before or after demineralization. The particles may be particulate or fibrous. The terms milling or grinding are not intended to be limited to production of particles of a specific type and may refer to production of particulate or fibrous particles. In certain embodiments, the particle size may be greater than 75 microns, such as ranging from about 100 to about 3000 microns, or from about 200 to about 2000 microns. After grinding, the bone particles may be sieved to select those particles of a desired size. In certain embodiments, the particles may be sieved though a 50 micron sieve, a 75 micron sieve, or a 100 micron sieve.

Providing Dry Bone Matrix

As previously discussed, DBM typically is dried, for example via lyophilization or solvent drying, to store and maintain the DBM in active condition for implantation. Moreover, each of these processes is thought to reduce the overall surface area structure of bone. As may be appreciated, the structural damage of the exterior surface reduces the overall surface area. Physical alterations to the surface and reduction in surface area can affect cell attachment, mobility, proliferation, and differentiation. The surface's affinity for growth factors and release kinetics of growth factors from the surface may also be altered.

Accordingly, in some embodiments, methods for drying bone to store and maintain the bone in active condition for implantation that maintains or increases the surface area of the bone are provided. In one embodiment, the bone matrix is treated using critical point drying (CPD) technique, thereby reducing destruction of the surface of the bone. While specific description is made to critical point drying, it is to be appreciated that, in alternative embodiments, super critical point treatment may be used. In various embodiments utilizing CPD, a percentage of collagen fibrils on the surface of the bone are non-denatured after drying to a residual moisture content of approximately 15% or less. In some embodiments, after drying, the bone matrix has a residual moisture content of approximately 8% or less. In some embodiments, after drying, the bone matrix has a residual moisture content of approximately 6% or less. In some embodiments, after drying, the bone matrix has a residual moisture content of approximately 6% or less. In some embodiments, after drying, the bone matrix has a residual moisture content of approximately 3% or less.

Evaporative drying and freeze drying of specimens can cause deformation and collapse of surface structures, leading to a decrease in surface area. Without wishing to be bound to a particularly theory, this deformation and structure is thought to be caused because, as a substance crosses the boundary from liquid to gas, the substance volatilizes such that the volume of the liquid decreases. As this happens, surface tension at the solid-liquid interface pulls against any structures to which the liquid is attached. Delicate surface structures tend to be broken apart by this surface tension. Such damage may be caused by the effects of surface tension on the liquid/gas interface. Critical point drying is a technique that avoids effects of surface tension on the liquid/gas interface by substantially preventing a liquid/gas interface from developing. Critical point or supercritical drying does not cross any phase boundary, instead passing through the supercritical region, where the distinction between gas and liquid ceases to apply. As a result, materials dehydrated using critical point drying are not exposed to damaging surface tension forces. When the critical point of the liquid is reached, it is possible to pass from liquid to gas without abrupt change in state. Critical point drying can be used with bone matrices to phase change from liquid to dry gas without the effects of surface tension. Accordingly, bone dehydrated using critical point drying can retain or increase at least some of the surface structure and therefore the surface area.

In some embodiments, critical point drying is carried out using carbon dioxide. However, other mediums such as freon, including Freon 13 (chlorotrifluoromethane), may be used. Generally, fluids suitable for supercritical drying include carbon dioxide (critical point 304.25 K at 7.39 MPa or 31.1° C. at 1072 psi or 31.2° C. and 73.8 bar) and freon (about 300 K at 3.5-4 MPa or 25 to 30° C. at 500-600 psi). Nitrous oxide has similar physical behavior to carbon dioxide, but is a powerful oxidizer in its supercritical state. Supercritical water is also a powerful oxidizer, partly because its critical point occurs at such a high temperature (374° C.) and pressure (3212 psi/647K and 22.064 MPa).

In some embodiments, the bone may be pretreated to remove water prior to critical point drying. Thus, in accordance with one embodiment, bone matrix is dried using carbon dioxide in (or above) its critical point status. After demineralization, bone matrix samples (in water) may be dehydrated to remove residual water content. Such dehydration may be, for example, through a series of graded ethanol solutions (for example, 20%, 50%, 70%, 80%, 90%, 95%, 100% ethanol in deionized water). In some embodiments, penetrating the tissue with a graded series of ethanol solutions or alcohols may be accomplished in an automated fashion. For example, pressure and vacuum could be used to accelerate penetration into the tissue.

In alternative embodiments, other means or procedures for removing water (drying or dehydrating) from the bone may be used. For example, the bone may be washed with other dehydrating liquids such as acetone to remove water, exploiting the complete miscibility of these two fluids. The acetone may then be washed away with high pressure liquid carbon dioxide.

In some embodiments, the dehydrated bone matrix is placed in a chamber within a critical point drying (CPD) apparatus and flushed with liquid $CO_2$ to remove ethanol (or other dehydrating liquid). Flushing with liquid $CO_2$ may be done one or more times. The temperature and/or pressure are then raised to the critical point (the critical point for $CO_2$ is reached at 31.2° C. and 73.8 bar). To perform critical point drying, the temperature and pressure may continue to be raised, for example to 40° C. with corresponding pressure of 85 bar. Thus, in some embodiments, the liquid carbon dioxide is heated until its pressure is at or above the critical point, at which time the pressure can be gradually released, allowing the gas to escape and leaving a dried product.

In certain embodiments, bone fibers processed using CPD have a BET surface area from about 1 to about 5 $m^2/gm$, a value 3 or 4 times greater than lyophilized bone fibers. In other embodiments, DBM fibers processed using CPD have a BET area surface from about 40 to about 100 $m^2/gm$, a value 100 times greater than when DBM fibers are lyophilized.

DBM dried with critical point carbon dioxide has increased biological activity and osteoinductivity when compared to DBM dried by lyophilization. In studies, as illustrated in Table 1 below, a typical amount of DBM was implanted in athymic mice in order to assess changes in osteoinductivity ("OI") of DBM that had been CPD treated by comparison to the same amount of lyophilized DBM.

TABLE 1

| Method | Surface area ($m^2/g$) | Bone formation (%, 2 wks) | OI at 2 wks | Bone formation (%, 4 wks) | OI at 4 wks |
|---|---|---|---|---|---|
| CPD | 95.8 | 16.78 | 3.25 | 42.48 | 4.00 |
| Lyophilization | 0.31 | 2.01 | 1.25 | 24.09 | 2.75 |

As illustrated in Table 1 above, unexpectedly, DBM fibers subjected to CPD showed an almost 100 fold increase in surface area by comparison to lyophilized DBM fibers. The increase in surface area was accompanied by an increase in osteoinductivity of almost three fold after 2 weeks and two fold after 4 weeks. The larger surface area of DBM fiber led to more and faster ectopic bone formation and higher OI score in an athymic rat osteoinductivity study. CPD treated DBM fibers displayed an 8 fold increase in bone formation at 2 weeks and a 2 fold increase in bone formation in 4 weeks when compared to lyophilized DBM fibers.

In a further embodiment, the critical point dried samples may further be treated, or alternatively be treated, with supercritical carbon dioxide (carbon dioxide above the critical point). Supercritical $CO_2$ may also be useful in viral inactivation. In some embodiments, thus, the bone matrix is placed in a supercritical $CO_2$ chamber and liquid $CO_2$ is introduced, for example, by an air pump. The temperature is raised to 105° C. with corresponding pressure about 485 bar. In alternative embodiments, other temperatures and/or pressures above the critical point of $CO_2$ may be used. The samples are soaked in supercritical $CO_2$ for a certain time and $CO_2$ is released. The resulting bone samples retain surface morphologies, hence surface area, and osteoinductivity after such treatment.

In yet a further embodiment, monolithic bone is demineralized and particulated before drying. Accordingly, the bone may be demineralized in monolithic pieces. The demineralized monolithic pieces may then be milled in a wet condition and critical point dried, for example using carbon dioxide as a medium.

In yet a further embodiment, monolithic bone is demineralized and dried before particulating (if done). Accordingly, the bone may be demineralized in monolithic pieces. The DBM is pressed in a wet condition and then critical point dried, for example using carbon dioxide as a medium. In alternatives of this embodiment, the demineralized and dried monolithic bone is not particulated and is processed as a monolithic implant.

Providing Demineralized Bone Material

Following shaving, milling or other technique whereby they are obtained, the bone material is subjected to demineralization in order to reduce its inorganic content to a very low level, in some embodiments, to not more than about 5% by weight of residual calcium and preferably to not more than about 1% by weight residual calcium. Demineralization of the bone material ordinarily results in its contraction to some extent.

Bone used in the methods described herein may be autograft, allograft, or xenograft. In various embodiments, the bone may be cortical bone, cancellous bone, or corticocancellous bone. While specific discussion is made herein to demineralized bone matrix, bone matrix treated in accordance with the teachings herein may be non-demineralized, demineralized, partially demineralized, or surface demineralized. The following discussion applies to demineralized, partially demineralized, and surface demineralized bone matrix. In one embodiment, the demineralized bone is sourced from bovine or human bone. In another embodiment, demineralized bone is sourced from human bone. In one embodiment, the demineralized bone is sourced from the patient's own bone (autogenous bone). In another embodiment, the demineralized bone is sourced from a different animal (including a cadaver) of the same species (allograft bone).

Any suitable manner of demineralizing the bone may be used. Demineralization of the bone material can be conducted in accordance with known conventional procedures. For example, in a preferred demineralization procedure, the bone material useful for the implantable composition of this application are subjected to an acid demineralization step that is followed by a defatting/disinfecting step. The bone material is immersed in acid over time to effect its demineralization. Acids which can be employed in this step include inorganic acids such as hydrochloric acid and organic acids such as peracetic acid, acetic acid, citric acid, or propionic acid. The depth of demineralization into the bone surface can be controlled by adjusting the treatment time, temperature of the demineralizing solution, concentration of the demineralizing solution, agitation intensity during treatment, and other applied forces such as vacuum, centrifuge, pressure, and other factors such as known to those skilled in the art. Thus, in various embodiments, the bone material may be fully demineralized, partially demineralized, or surface demineralized.

After acid treatment, the bone is rinsed with sterile water for injection, buffered with a buffering agent to a final predetermined pH and then finally rinsed with water for injection to remove residual amounts of acid and buffering agent or washed with water to remove residual acid and thereby raise the pH. Following demineralization, the bone material is immersed in solution to effect its defatting. A preferred defatting/disinfectant solution is an aqueous solution of ethanol, the ethanol being a good solvent for lipids and the water being a good hydrophilic carrier to enable the solution to penetrate more deeply into the bone. The aqueous ethanol solution also disinfects the bone by killing vegetative microorganisms and viruses. Ordinarily at least about 10 to 40 weight percent by weight of water (i.e., about 60 to 90 weight percent of defatting agent such as alcohol) should be present in the defatting/disinfecting solution to produce optimal lipid removal and disinfection within the shortest period of time. The preferred concentration range of the defatting solution is from about 60 to 85 weight percent alcohol and most preferably about 70 weight percent alcohol. Further in accordance with this application, the demineralized bone material can be used immediately for preparation of the implant composition or it can be stored under aseptic conditions, advantageously in a critical point dried state prior to such preparation. In a preferred embodiment, the bone material can retain some of its original mineral content such that the composition is rendered capable of being imaged utilizing radiographic techniques.

Providing Demineralized Bone Matrix

In various embodiments, this application also provides bone matrix compositions which comprises CPD fibers. DBM includes the collagen matrix of the bone together with acid insoluble proteins including bone morphogenic proteins (BMPs) and other growth factors. It can be formulated for use as granules, gels, sponge material or putty and can be freeze-dried for storage. Sterilization procedures used to protect from disease transmission may reduce the activity of beneficial growth factors in the DBM. DBM provides an initial osteoconductive matrix and exhibits a degree of osteoinductive potential, inducing the infiltration and differentiation of osteoprogenitor cells from the surrounding tissues.

DBM preparations have been used for many years in orthopedic medicine to promote the formation of bone. For example, DBM has found use in the repair of fractures, in the fusion of vertebrae, in joint replacement surgery, and in treating bone destruction due to underlying disease such as rheumatoid arthritis. DBM is thought to promote bone formation in vivo by osteoconductive and osteoinductive processes. The osteoinductive effect of implanted DBM compositions is thought to result from the presence of active growth factors present on the isolated collagen-based matrix. These factors include members of the TGF-β, IGF, and BMP protein families. Particular examples of osteoinductive factors include TGF-β, IGF-1, IGF-2, BMP-2, BMP-7, parathyroid hormone (PTH), and angiogenic factors. Other osteoinductive factors such as osteocalcin and osteopontin are also likely to be present in DBM preparations as well. There are also likely to be other unnamed or undiscovered osteoinductive factors present in DBM.

In various embodiments, the DBM provided in the methods described in this application is prepared from elongated bone fibers which have been subjected to critical point drying. The elongated CPD bone fibers employed in this application are generally characterized as having relatively high average length to average width ratios, also known as the aspect ratio. In various embodiments, the aspect ratio of the elongated bone fibers is at least from about 50:1 to about at least about 1000:1. Such elongated bone fibers can be readily obtained by any one of several methods, for example, by milling or shaving the surface of an entire bone or relatively large section of bone.

In other embodiments, the length of the fibers can be at least about 3.5 cm and average width from about 20 mm to about 1 cm. In various embodiments, the average length of the elongated fibers can be from about 3.5 cm to about 6.0 cm and the average width from about 20 mm to about 1 cm. In other embodiments, the elongated fibers can have an average length be from about 4.0 cm to about 6.0 cm and an average width from about 20 mm to about 1 cm.

In yet other embodiments, the diameter or average width of the elongated fibers is, for example, not more than about 1.00 cm, not more than 0.5 cm or not more than about 0.01 cm. In still other embodiments, the diameter or average width of the fibers can be from about 0.01 cm to about 0.4 cm or from about 0.02 cm to about 0.3 cm.

In another embodiment, the aspect ratio of the fibers can be from about 50:1 to about 950:1, from about 50:1 to about 750:1, from about 50:1 to about 500:1, from about 50:1 to about 250:1; or from about 50:1 to about 100:1. Fibers according to this disclosure can advantageously have an aspect ratio from about 50:1 to about 1000:1, from about 50:1 to about 950:1, from about 50:1 to about 750:1, from about 50:1 to about 600:1, from about 50:1 to about 350:1, from about 50:1 to about 200:1, from about 50:1 to about 100:1, or from about 50:1 to about 75:1.

To prepare the osteogenic DBM, a quantity of fibers is combined with a biocompatible carrier to provide a demineralized bone matrix.

Providing a Carrier

Generally, materials for the carrier may be biocompatible in vivo and optionally biodegradable. In some uses, the carrier acts as a temporary scaffold until replaced completely by new bone. Suitable carriers can be any number of compounds and/or polymers, such as polymer sugars, proteins, long chain hydrophilic block copolymers, reverse phase block copolymers, hyaluronic acid, polyuronic acid, mucopolysaccharide, proteoglycan, polyoxyethylene, surfactants, including the pluronics series of nonionic surfactants, and peptide thickener. Suggested classes of biocompatible fluid carrier would include polyhydroxy compound, polyhydroxy ester, fatty alcohol, fatty alcohol ester, fatty acid, fatty acid ester, liquid silicone, mixtures thereof, and the like. Settable materials may be used, and they may set up either in situ, or prior to implantation. The bone fibers and carrier (or delivery or support system) together form an osteoimplant useful in clinical applications.

Examples of suitable biocompatible fluid carrier include, but are not limited to:

(i) Polyhydroxy compound, for example, such classes of compounds as the acyclic polyhydric alcohols, non-reducing sugars, sugar alcohols, sugar acids, monosaccharides, disaccharides, water-soluble or water dispersible oligosaccharides, polysaccharides and known derivatives of the foregoing. Specific polyhydroxy compounds include, 1,2-propanediol, glycerol, 1,4,-butylene glycol trimethylolethane, trimethylolpropane, erythritol, pentaerythritol, ethylene glycols, diethylene glycol, triethylene glycol, tetraethylene glycol, propylene glycol, dipropylene glycol; polyoxyethylene-polyoxypropylene copolymer, for example, of the type known and commercially available under the trade names Pluronic and Emkalyx; polyoxyethylene-polyoxypropylene block copolymer, for example, of the type known and commercially available under the trade name Poloxamer; alkylphenolhydroxypolyoxyethylene, for example, of the type known and commercially available under the trade name Triton, polyoxyalkylene glycols such as the polyethylene glycols, xylitol, sorbitol, mannitol, dulcitol, arabinose, xylose, ribose, adonitol, arabitol, inositol, fructose, galactose, glucose, mannose, sorbose, sucrose, maltose, lactose, maltitol, lactitol, stachyose, maltopentaose, cyclomaltohexaose, carrageenan, agar, dextran, alginic acid, guar gum, gum tragacanth, locust bean gum, gum arabic, xanthan gum, amylose, mixtures of any of the foregoing, and the like.

(ii) Polyhydroxy ester, for example, liquid and solid monoesters and diesters of glycerol can be used to good effect, the solid esters being dissolved up in a suitable vehicle, for example, propylene glycol, glycerol, polyethylene glycol of 200-1000 molecular weight. Liquid glycerol esters include monacetin and diacetin and solid glycerol esters include such fatty acid monoesters of glycerol as glyceryl monolaurate, glyceryl monopalmitate, glyceryl monostearate. In various embodiments, the carrier herein comprises glyceryl monolaurate dissolved in glycerol or a 4:1 to 1:4 weight mixtures of glycerol and propylene glycol, poly(oxyalkylene) glycol ester, and the like.

(iii) Fatty alcohol, for example primary alcohols, usually straight chain having from 6 to 13 carbon atoms, including caproic alcohol, caprylic alcohol, undecyl alcohol, lauryl alcohol, and tridecanol.

(iv) Fatty alcohol ester, for example, ethyl hexyl palmitate, isodecyl neopentate, octadodecyl benzoate, diethyl hexyl maleate, and the like.

(v) Fatty acid having from 6 to 11 carbon atoms, for example, hexanoic acid, heptanoic acid, octanoic acid, decanoic acid and undecanoic acid.

(vi) Fatty acid ester, for example, polyoxyethylene-sorbitan-fatty acid esters, for example, mono- and tri-lauryl, palmityl, stearyl, and oleyl esters including of the type available under the trade name Tween from Imperial Chemical Industries; polyoxyethylene fatty acid esters including polyoxyethylene stearic acid esters of the type known and commercially available under the trade name MA; propylene glycol mono- and di-fatty acid esters such as propylene glycol dicaprylate; propylene glycol dilaurate, propylene glycol hydroxy stearate, propylene glycol isostearate, propylene glycol laureate, propylene glycol ricinoleate, propylene glycol stearate, and propylene glycol caprylic-capric acid diester available under the trade name Miglyol; mono-, di-, and mono/di-glycerides, such as the esterification products of caprylic or caproic acid with glycerol, for example, of the type known and commercially available under the trade name lmwitor; sorbitan fatty acid esters, or of the type known and commercially available under the trade name Span, including sorbitan-monolauryk-monopalmityl, -monostearyl, -tristearyl, -monooleyl and triolcylesters; monoglycerides, for example, glycerol monooleate, glycerol monopalmitate and glycerol monostearate, for example as known and commercially available under the trade names Myvatex, Myvaplex and Myverol, and acetylated, for example, mono- and di-acetylated monoglycerides, for example, as known and commercially available under the trade name Myvacet; isobutyl tallowate, n-butylstearate, n-butyl oleate, and n-propyl oleate.

(vii) Liquid silicone, for example, polyalkyl siloxanes such as polymethyl siloxane and poly(dimethyl siloxane) and polyalkyl arylsiloxane.

In some embodiments of the implantable composition of this application, the liquid carrier is a liquid polyhydroxy compound, liquid polyhydroxy compound derivative, liquid solution of solid polyhydroxy compound, liquid solution of solid polyhydroxy compound derivative or mixtures thereof. If necessary or desirable, in some embodiments, the liquid carrier can be dissolved or diluted with an appropriate solvent such that when combined with the demineralized bone fibers described herein a composition capable of being shaped or packed into a coherent mass which retains its shape and volume over the relatively long term, until the bone formation and remodeling process is completed, is provided. Thus, the polyhydroxy compound or polyhydroxy derivatives can be a liquid in the pure or highly concentrated state at ambient temperature, from about 15° C. to about 50° C., or it can be a solid or semi-solid at this temperature in which case it becomes necessary to dissolve the material in a solvent such as water, physiological saline, ethanol, glycerol, glucose, propylene glycol, polyethylene glycol of from 200-1000 molecular weight, or polyvinyl alcohol. In other embodiments, the liquid carrier can be made up of one or more liquid polyhydroxy compounds or derivatives in solution with one or more solid polyhdroxy compounds or derivatives.

The osteoinductive or biologically active composition may be configured to be moldable, extrudable, or substantially solid. The osteoinductive or biologically active composition may be configured to substantially retain its shape in water for a period of time. The osteoinductive or biologically active composition may form an osteoimplant useful in clinical applications. Suitable carriers may include surface demineralized bone; mineralized bone; nondemineralized cancellous scaffolds; demineralized cancellous scaffolds; cancellous chips; particulate, demineralized, guanidine extracted, species-specific (allogenic) bone; specially treated particulate, protein extracted, demineralized, xenogenic bone; collagen; synthetic hydroxyapatites; synthetic calcium phosphate materials; tricalcium phosphate, sintered hydroxyapatite, settable hydroxyapatite; polylactide polymers; polyglycolide polymers, polylactide-co-glycolide copolymers; tyrosine polycarbonate; calcium sulfate; collagen sheets; settable calcium phosphate; polymeric cements; settable poly vinyl alcohols, polyurethanes; resorbable polymers; and other large polymers; liquid settable polymers; and other biocompatible settable materials. The carrier may further comprise a polyol (including glycerol or other polyhydroxy compound), a polysaccharide (including starches), a hydrogel (including alginate, chitosan, dextran, pluronics, N,O-carboxymethylchitosan glucosamine (NOCC)), hydrolyzed cellulose, or a polymer (including polyethylene glycol). In embodiments wherein chitosan is used as a carrier, the chitosan may be dissolved using known methods including in water, in mildly acidic aqueous solutions, in acidic solutions.

The carrier may further comprise a hydrogel such as hyaluronic acid, dextran, pluronic block copolymers of polyethylene oxide and polypropylene, and others. Suitable polyhydroxy compounds include such classes of compounds as acyclic polyhydric alcohols, non-reducing sugars, sugar alcohols, sugar acids, monosaccharides, disaccharides, water-soluble or water dispersible oligosaccharides, polysaccharides and known derivatives of the foregoing. An example carrier comprises glyceryl monolaurate dissolved in glycerol or a 4:1 to 1:4 weight mixture of glycerol and propylene glycol. Settable materials may be used, and they may set up either in situ, or prior to implantation. Optionally, xenogenic bone powder carriers also may be treated with proteases such as trypsin. Xenogenic carriers may be treated with one or more fibril modifying agents to increase the intraparticle intrusion volume (porosity) and surface area. Useful agents include solvents such as dichloromethane, trichloroacetic acid, acetonitrile and acids such as trifluoroacetic acid and hydrogen fluoride. The choice of carrier may depend on the desired characteristics of the composition. In some embodiments, a lubricant, such as water, glycerol, or polyethylene glycol may be added.

Any suitable shape, size, and porosity of carrier may be used. In some embodiments, the carrier may be settable and/or injectable. Such carrier may be, for example, a polymeric cement, a suitable settable calcium phosphate, a settable poly vinyl alcohol, a polyurethane, or a liquid settable polymer. Hydrogel carriers may additionally impart improved spatial properties, such as handling and packing properties, to the osteoconductive composition. An injectable carrier may be desirable where the composition is used with a containment device. In addition, selected materials must be biocompatible in vivo and optionally biodegradable. In some uses, the carrier acts as a temporary scaffold until replaced by new bone. Polylactic acid (PLA), polyglycolic acid (PGA), and various combinations have different dissolution rates in vivo. In bone, the dissolution rates can vary according to whether the composition is placed in cortical or trabecular bone.

In certain embodiments, the carrier may comprise a shape-retaining solid made of loosely adhered particulate material with collagen. It may alternatively comprise a molded, porous solid, a monolithic solid, or an aggregate of close-packed particles held in place by surrounding tissue. Masticated muscle or other tissue may also be used. Large allogenic bone implants may act as a carrier, for example where their marrow cavities are cleaned and packed with DBM and, optionally, the osteoinductive factors.

In various embodiments, the carrier comprises an osteoinductive material such as a mineralized particulated material, osteoinductive growth factors, or partially demineralized bone. The mineralized particulated material may be TCP, hydroxyapatite, mineral recovered from bone, cancellous chips, cortical chips, surface demineralized bone, or other material. The osteoinductive material may be combined with a further carrier such as starch or glycerol. Accordingly, in some embodiments, the bone matrix may act as a carrier for the tissue-derived extract.

Where, in a particular implantable composition, the fibrous and/or non-fibrous elements exhibit a tendency to quickly or prematurely separate from the carrier component or to otherwise settle out from the composition such that application of a fairly homogeneous composition is rendered difficult or inconvenient, it can be advantageous to include within the composition an optional substance whose thixotropic characteristics prevent or reduce this tendency. Thus, for example, where the carrier component is glycerol and separation of fibrous and/or non-fibrous bone elements occurs to an excessive extent where a particular application is concerned, a thixotropic agent such as a solution of polyvinyl alcohol, polyvinylpyrrolidone, cellulosic ester such as hydroxypropyl methylcellulose, carboxyl methylcellulose, pectin, food-grade texturizing agent, gelatin, dextran, collagen, starch, hydrolyzed polyacrylonitrile, hydrolyzed polyacrylamide, polyelectrolyte such as polyacrylic acid salt, hydrogels, chitosan, other materials that can suspend the fibrous and/or non-fibrous elements, can be combined with the carrier in an amount sufficient to significantly improve the suspension-keeping characteristics of the composition.

Preparing a DBM Composition

To prepare a DBM composition according to one or more embodiments of this application, a quantity of demineralized bone fibers prepared as described above and subjected to critical point drying is combined with water or any other appropriate, biocompatible liquid to form a smooth, flowable, cohesive paste. The resultant implantable composition may be molded or injected into any desired shape and retains its shape, even when submersed in water, saline, or other aqueous solution. An additional benefit of the DBM fibers is that the resultant paste is injectable through an 18-gauge needle.

The liquid may be any biocompatible liquid, including water, saline solution, buffered solutions, serum, bone marrow aspirant, blood, platelet-rich plasma and the like and mixtures thereof. Some biocompatible liquids suitable for use with the short DBM fibers, such as serum, bone marrow aspirant and blood, additionally contain osteoinductive factors that will promote bone growth at the site to which the composition is applied.

In various embodiments, an implantable bone composition having an enhanced osteoinductivity and/or osteoconductivity is provided. Critical point drying (CPD) increases the surface area of allograft implants significantly. The increase in surface area facilitates bone formation, allograft implant remodeling and integration to host bone.

The new bone composition comprises a higher surface area which can induce significantly more and faster bone formation. Allograft implants with high surface area can improve the integration between implant and host bone.

In various embodiments, the implantable bone composition comprises demineralized bone matrix dried at critical point of carbon dioxide. CPD fibers of demineralized bone matrix comprise a surface area having a BET value from about 40 $m^2/gm$ to about 100 $m^2/gm$, which is about 100 times higher surface area than a corresponding vacuum dried or lyophilized DBM fibers.

In various embodiment, there is an implantable composition comprising demineralized bone matrix dried with carbon dioxide at its critical point that has an osteoinductivity of about 4.00.

Providing Optional Additives

If desired, the fibrous and/or non-fibrous bone elements of this application can be modified in one or more ways. In various embodiments, any of a variety of medically and/or surgically useful optional substances can be incorporated in, or associated with, the bone elements before, during, or after preparation of the implantable composition. Thus, in some embodiments, one or more of such substances can be introduced into the bone elements, for example, by soaking or immersing the bone elements in a solution or dispersion of the desired substance(s), by adding the substance(s) to the carrier component of the implantable composition or by adding the substance(s) directly to the implantable composition.

Medically/surgically useful substances which can be readily combined with the bone fibers, fluid carrier and/or implantable composition of this application include, for example, collagen, insoluble collagen derivatives, hydroxyapatite, and soluble solids and/or liquids dissolved therein, for example, antiviricides, particularly those effective against HIV and hepatitis; antimicrobials and/or antibiotics such as erythromycin, bacitracin, neomycin, penicillin, polymyxin B, tetracyclines, viomycin, chloromycetin and streptomycins, cefazolin, ampicillin, azactam, tobramycin, clindamycin and gentamycin; amino acids, peptides, vitamins, inorganic elements, inorganic compounds, cofactors for protein synthesis, hormones; endocrine tissue or tissue fragments; synthesizers; enzymes such as collagenase, peptidases, oxidases; polymer cell scaffolds with paraenchymal cells; angiogenic drugs and polymeric carriers containing such drugs; collagen lattices; biocompatible surface active agents; antigenic agents; cytoskeletal agents; cartilage fragments, living cells such as chondrocytes, bone marrow cells, mesenchymal stem cells, natural extracts, tissue transplants, bioadhesives, bone morphogenic proteins (BMPs), transforming growth factor (TGF-beta), insulin-like growth factor (IGF-1) (IGF-2), platelet derived growth factor (PDGF), fibroblast growth factors (FGF), vascular endothelial growth factor (VEGF), angiogenic agents, bone promoters, cytokines, interleukins, genetic material, genes encoding bone promoting action, cells containing genes encoding bone promoting action; growth hormones such as somatotropin; bone digestors; antitumor agents; fibronectin; cellular attractants and attachment agents; immunosuppressants; permeation enhancers, for example, fatty acid esters such as laureate, myristate and stearate monesters of polyethylene glycol, surface active agents, enamine derivatives, α-keto aldehydes; nucleic acids; epidermal growth factor (EGF); all collagen types (not just type 1); non-collagenous proteins such as osteopontin, osteonectine, bone sialo proteins, vitronectin, thrombospondin, proteoglycans, decorin, biglycan, aggrecan, versican, tenascin, matrix gla protein hyaluronan; soluble and insoluble components of the immune system, soluble and insoluble receptors including truncated forms, soluble, insoluble and cell surface bound ligands including truncated forms; chemokines, bioactive compounds that are endocytosed; compounds capable of altering the membrane potential of cells, compounds capable of altering the monovalent and divalent cation/anion channels of cells; bone resorption inhibitors and stimulators; angiogenic and mitogenic factors; bioactive factors that inhibit and stimulate second messenger molecules; integrin adhesion molecules; clotting factors; externally expanded autograft or xenograft cells and any combinations thereof. The amounts of such optionally added substances can vary widely with optimum levels being readily determined in a specific case by routine experimentation.

The demineralized bone matrix prepared with the CPD bone fibers described herein may comprise a number of materials in combination, some or all of which may be in the form of fibers and/or particles. The matrix may comprise calcium phosphates. Driessens et al. "Calcium phosphate bone cements," Wise, D. L., Ed., Encyclopedic Handbook of Biomaterials and Bioengineering, Part B, Applications New York: Marcel Decker; Elliott, Structure and Chemistry of the Apatites and Other Calcium Phosphates Elsevier, Amsterdam, 1994, each of which is incorporated by reference. Calcium phosphate matrices include, but are not limited to, dicalcium phosphate dihydrate, monetite, tricalcium phosphate, tetracalcium phosphate, hydroxyapatite, nanocrystalline hydroxyapatite, poorly crystalline hydroxyapatite, substituted hydroxyapatite, and calcium deficient hydroxyapatites. In some embodiments, the bone fibers may be added to a carrier.

Implantable DBM compositions have been used for many years in orthopedic medicine to promote the formation of bone. For example, DBM compositions have found use in the repair of fractures, in the fusion of vertebrae, in joint replacement surgery, and in treating bone destruction due to underlying disease such as rheumatoid arthritis. DBM is thought to promote bone formation in vivo by osteoconductive and osteoinductive processes. The osteoinductive effect of implanted DBM compositions is thought to result from the presence of active growth factors present on the isolated collagen-based matrix. These factors include members of the TGF-β, IGF, and BMP protein families. Particular examples of osteoinductive factors include TGF-β, IGF-1, IGF-2, BMP-2, BMP-7, parathyroid hormone (PTH), and angiogenic factors. Other osteoinductive factors such as osteocalcin and osteopontin are also likely to be present in DBM preparations as well. There are also likely to be other unnamed or undiscovered osteoinductive factors present in DBM.

In some embodiments, the demineralized bone may be further treated to affect properties of the bone. For example, the DBM may be treated to disrupt the collagen structure of the DBM. Such treatment may comprise collagenase treatment, heat treatment, mechanical treatment, or other. While demineralized bone is specifically discussed herein, in some embodiments, the teachings herein may be applied to non-demineralized bone, to partially demineralized bone, or to surface demineralized bone.

In some embodiments, biological activities of the bone matrix may be increased. Accordingly, the bone matrix, and compositions formed from the bone matrix, may variously be referred to as biologically active and/or, in some cases, osteoinductive. The biological activities of the bone composition provided herein that may be increased include but are not limited to osteoinductive activity, osteogenic activity, chondrogenic activity, wound healing activity, neurogenic activity, contraction-inducing activity, mitosis-inducing activity, differentiation-inducing activity, chemotactic activity, angiogenic or vasculogenic activity, exocytosis or endocytosis-inducing activity, or other cell or biological activity. It will be appreciated that bone formation processes frequently include a first stage of cartilage formation that creates the basic shape of the bone, which then becomes mineralized (endochondral bone formation). Thus, in many instances, chondrogenesis may be considered an early stage of osteogenesis, though of course it may also occur in other contexts.

In accordance with various embodiments, the bone matrix provided herein may be used with growth factors, extracts, peptide hormones, or other additives to increase the osteoinductive capacity or that otherwise encourage cell or biological activity of the bone matrix or to impart other benefits to the bone matrix. It will be appreciated that the amount of additive used will vary depending upon the type of additive, the specific activity of the particular additive preparation employed, and the intended use of the composition. The desired amount is readily determinable by the user.

Any of a variety of medically and/or surgically useful optional substances can be incorporated in, or associated with, the osteoinductive factors either before, during, or after preparation of the osteoinductive or biologically active composition. Thus, for example when CPD demineralized bone fibers of this application are used to form the material, one or more of such substances may be introduced into the CPD demineralized bone fibers, for example, by soaking or immersing these bone fibers in a solution or dispersion of the desired substance(s).

In one embodiment, a tissue-derived extract may be added to the bone matrix. U.S. published patent application No. 2009/0130173 discloses such extracts and addition of such extracts to DBM and is incorporated herein by reference. For example, a tissue-derived extract or partially demineralized bone may be added to the bone matrix. The extract may be derived from any suitable tissue, such as bone, bladder, kidney, brain, skin, or connective tissue. Further, the extract may be derived in any suitable manner. The extract may be allogeneic, autogeneic, xenogeneic, or transgenic. In embodiments wherein the extract is bone-derived, the bone may be cortical, cancellous, or corticocancellous and may be demineralized, partially demineralized, or mineralized. In some embodiments, the extract may comprise demineralized bone, partially demineralized bone, mineral derived from bone, or collagen derived from bone. In some embodiments, the tissue-derived extract may be a protein extract.

Bone regeneration involves a multitude of cells, for example, cartilage, fibroblasts, endothelial cells besides osteoblasts. Accordingly, the bone matrix composition may be used to deliver stem cells, which offers the potential to give rise to different types of cells in the bone repair process. In one embodiment, the bone matrix composition further comprises a cell such as an osteogenic cell or a stem cell.

In various embodiments, the additive may comprise radiopaque substances, angiogenesis promoting materials, bioactive agents, osteoinducing agents, or other. Such materials would include without limitation barium sulfate, iodine-containing compounds, titanium and mineralized bone.

In certain embodiments, the additive is adsorbed to or otherwise associated with the bone matrix. The additive may be associated with the bone matrix through specific or non-specific interactions, or covalent or noncovalent interactions. Examples of specific interactions include those between a ligand and a receptor, an epitope or an antibody. Examples of nonspecific interactions include hydrophobic interactions, electrostatic interactions, magnetic interactions, dipole interactions, van der Waals interactions, or hydrogen bonding. In certain embodiments, the additive is attached to the bone matrix composition, for example, to the carrier, using a linker so that the additive is free to associate with its receptor or site of action in vivo. In other embodiments the additive is either covalently or non-covalently attached to the carrier. In certain embodiments, the additive may be attached to a chemical compound such as a peptide that is recognized by the carrier. In another embodiment, the additive is attached to an antibody, or fragment thereof, that recognizes an epitope found within the carrier. In certain embodiments at least additives are attached to the osteoimplant. In other embodiments at least three additives are attached to the osteoinductive or biologically active composition. An additive may be provided within the osteoinductive or biologically active composition in a sustained release format. For example, the additive may be encapsulated within biodegradable polymer nanospheres, or microspheres.

Flow additives according to this application can include, but are not limited to, small molecule organic compounds, polymeric/oligomeric materials, and solutions thereof. In some embodiments, when added to the implantable composition containing the bone fibers the viscosity thereof should be sufficiently changed to allow flow through a syringe needle of about 8-gauge or greater (greater number gauges of syringe needles have smaller diameters, thus requiring lower threshold viscosity through which they may flow), preferably of about 12-gauge or greater, for example of about 14-gauge or greater, of about 15-gauge or greater, or of about 18-gauge or greater. Sufficient flow can be understood, in terms of syringe needles, to result in an injection force of not more than 50 pounds, preferably not more than 40 pounds. In another embodiment, the flow additive modifies the viscosity of the composition to which it is added such that the composition is capable of flowing through a syringe needle having a gauge size from about 8 to about 18, alternately from about 8 to about 15, from about 12 to about 18, or from about 12 to about 15.

When present, the amount of flow additive that can be added to the composition can be from about 0.01% to about 1.5% by weight of the fiber composition from about 0.1% to about 1% by weight, or from about 0.05% to about 1% by weight. In an alternate embodiment, the amount of flow additive can be from about 1.5% to about 5% by weight of the fiber composition. In a preferred embodiment, the flow additive, when used, is present in an amount of about 0.5% by weight of the composition.

Suitable examples of flow additives can include, but are in no way limited to, hyaluronic acid; hyaluronate salts such as sodium, potassium, lithium, or the like, or a combination thereof; alginate salts such as sodium, potassium, lithium, or the like; starch compounds, which can be present in its natural form, in a destructured form, or in any number of chemically modified derivative forms (for example, alkyoxylated derivatives, esterified derivatives, ionically modified starches, oxidized starches, grafted starches, crosslinked starches, or the like, or mixtures thereof); saturated, monounsaturated, and/or polyunsaturated oils, such as those extracted or isolated from plant and/or animal sources, including, but not limited to, sunflower, safflower, peanut, castor bean, sesame, coconut, soybean, corn, canola, olive, vegetable, palmitins, stearins, oleins, and the like, or derivatives or combinations thereof, as naturally extracted, as synthesized, or as modified or processed in some way, partially or fully hydrogenated, partially or fully dehydrogenated, partially or fully saponified, partially or fully acidified, partially halogenated, or the like; a wax including, but not limited to, hydrocarbon waxes (for example, polyolefin waxes, such as polyethylene wax, polypropylene wax, and the like, or copolymers thereof), oligoester waxes, monoester waxes, oligoether waxes, monoether waxes, and the like, or combinations thereof, as naturally extracted, as synthesized, or as modified or processed in some way, partially or fully hydrogenated, partially or fully dehydrogenated, partially or fully saponified, partially or fully acidified, partially halogenated, or the like; cellulosic compounds, including, but not limited to, native or synthetic cellulose, cotton, regenerated cellulose (for example, rayon, cellophane, or the like), cellulose acetate, cellulose propionate, cellulose butyrate, cellulose acetate-propionate, cellulose acetate-butyrate, cellulose propionate-butyrate, cellulose nitrate, methyl cellulose, ethyl cellulose, carboxymethyl cellulose, carboxyethyl cellulose, cellulose salts, and combinations or copolymers thereof, as naturally extracted, as synthesized, or as modified or processed in some way, including partially or fully esterified, partially or fully nitrated, partially or fully regenerated, partially or fully etherified, partially or fully acidified, partially or fully acid-neutralized, or the like, or combinations thereof; surface-active biomolecules or (co)polymers; poly(ethylene glycol) and/or poly(ethylene oxide) oligomers, homopolymers, or copolymers; autologous substances such as autologous bone marrow aspirates, autologous blood substances, or the like, or a combination thereof; heterologous substances such as allogeneic bone marrow aspirates, xenogenic bone marrow aspirates, allogeneic blood substances, xenogenic blood substances, or the like, or a combination thereof; or the like, or combinations thereof. In a preferred embodiment, the flow additive comprises hyaluronic acid and/or a hyaluronate salt. In another preferred embodiment, the flow additive comprises sodium hyaluronate. In an alternate embodiment, the flow additive can include chondroitin, glucosamine, hyaluronic acid, a salt thereof, or a mixture thereof.

In one or more embodiments, an additive is included in the DBM composition to further modify the handling characteristics of the composition, such as viscosity and moldability. The additive may be a biocompatible polymer, such as a water-soluble cellulosic, or a natural polymer, such as gelatin. The additive may be added to either the dry DBM component or the liquid component. The additive may be used to at least partially coat the DBM fibers prior to combining them with the liquid carrier. Non-limiting examples of additives suitable for use in the DBM composition include gelatin, carboxymethyl cellulose, hydroxypropyl methylcellulose, methylcellulose, hydroxyethyl cellulose, other cellulose derivatives, alginate, hyaluronic acid, sodium salts, polyvinyl pyrrolidones, polyvinyl alcohol, arabic gum, guar gum, xantham gum, chitosans, and poloxamers.

As previously indicated, the implantable composition of this disclosure can be freshly prepared just by mixing desired quantities of the CPD demineralized fibrous bone elements, fluid carrier and optional component(s), if any, in any suitable sequence of separate mixing, adsorption, rehydration or drying operations or all at once. Thus, the CPD demineralized fibrous bone elements can be mixed with the optional ingredients(s) and thereafter combined with the fluid carrier component, the demineralized fibrous bone elements can be mixed with the fluid carrier followed by addition of the optional ingredient(s) or the optional ingredients can be added to the fluid carrier followed by addition of the demineralized fibrous bone elements. Variations of these and other sequences of mixing are, of course, possible. In various embodiments, the implantable composition can include non-fibrous bone elements. In other embodiments, the fibrous elements and fluid carrier are mixed substantially simultaneously such that the fibrous elements of the implantable composition are entangled and the non-fibrous bone elements are thoroughly mixed in the entangled fibrous bone elements.

In various embodiments, when the DBM contains elongated fibers which have been critically point dried, the resulting DBM also contains enhanced osteoconductivity. The elongated CPD fibers disclosed herein are naturally more osteoconductive than non-fibrous elements, as cells, for example, osteoclasts and osteoblasts, can travel along the length of the fiber farther and with greater orientation to gain access to the composite interior of the bone demineralized matrix. The entangled fiber network provides a continuous pathway for improved cellular access over the fibers of implantable composition utilized in DBM and as a result an improvement in osteoconductivity is, therefore, expected.

The amount of demineralized CPD bone fibers which can be incorporated into the implantable composition can vary widely with amounts of about 99% weight, about 95% by weight, about 90% by weight, about 85% by weight 70% by weight. In various embodiments, the amount of the non-fibrous bone elements which can be incorporated into the implantable composition can vary widely with amounts from about 10 to about 90 weight percent, and preferably from about 20 to about 70 weight percent. The ratio of fibrous to non-fibrous bone elements can vary between about 0.2:1 to about 1:0.2. The balance of the composition being made up of fluid carrier and optional ingredient(s), if any.

The bone matrix composition may be completely insoluble or may be slowly solubilized after implantation. Following implantation, the composition may resorb or degrade, remaining substantially intact for at least one to seven days, or for two or four weeks or longer and often longer than 60 days. The composition may thus be resorbed prior to one week, two weeks, three weeks, or other, permitting the entry of bone healing cells.

Preparing an Implant

The bone matrix compositions provided herein may be used to form an osteoinductive or biologically active osteoimplant. The osteoimplant resulting from the bone matrix, additive, and/or carrier may be flowable, have a putty consistency, may be shaped or molded, and/or may be deformable. The osteoimplant may assume a determined or regular form or configuration such as a sheet, plate, disk, tunnel, cone, or tube, to name but a few. Prefabricated geometry may include, but is not limited to, a crescent apron for single site use, an I-shape to be placed between teeth for intra-bony defects, a rectangular bib for defects involving both the buccal and lingual alveolar ridges, neutralization plates, reconstructive plates, buttress plates, T-buttress plates, spoon plates, clover leaf plates, condylar plates, compression plates, bridge plates, or wave plates. Partial tubular as well as flat plates can be fabricated from the osteoimplant. Such plates may include such conformations as, for example, concave contoured, bowl shaped, or defect shaped. The osteoimplant can be machined or shaped by any suitable mechanical shaping means. Computerized modeling can provide for the intricately-shaped three-dimensional architecture of an osteoimplant custom-fitted to the bone repair site with great precision. In embodiments wherein the osteoimplant is shaped or moldable, as a result of the inclusion of the demineralized bone fibers of this application the implant can retain coherence or cohesiveness in fluids.

In certain embodiments, the osteoinductive or biologically active bone matrix composition may be subjected to a configuring step to form an osteoimplant. The configuring step can be employed using conventional equipment known to those skilled in the art to produce a wide variety of geometries, e.g., concave or convex surfaces, stepped surfaces, cylindrical dowels, wedges, blocks, screws, and the like.

To facilitate on-site preparation and/or usage of the composition herein, the demineralized fibrous bone elements and non-fibrous bone elements, preferably in lyophilized or frozen form, and fluid carrier (the latter containing one or more optional ingredients such as those identified above) can be stored in separate packages or containers under sterile conditions and brought together in intimate admixture at the moment of use for immediate application to an osseous defect site employing any suitable means such as spatula, forceps, syringe, tamping device, and the like. Alternatively, the implant composition can be prepared well in advance and stored under sterile conditions until required for use. When the implant composition is prepared well in advance it is preferably subjected to critical point drying prior to packaging for storage. In some embodiments, the composition described herein can be combined with autograft bone marrow aspirate, autograft bone, preparations of selected autograft cells, autograft cells containing genes encoding bone promoting action prior to being placed in a defect site. In various embodiments, the implant composition is packaged already mixed and ready for use in a suitable container, such as for example, syringe, resealable non-toxic bottle, a bag mesh or pouch or is provided as a kit which can be prepared at a surgeon's direction when needed.

In some embodiments, the implantable composition can be delivered within a porous mesh that will provide targeted and contained delivery. The polymer mesh can comprise a polymer (such as polyalkylenes (e.g., polyethylenes, polypropylenes), polyamides, polyesters, polyurethanes, poly(lactic acid-glycolic acid), poly(lactic acid), poly(glycolic acid), poly(glaxanone), poly(orthoesters), poly(pyrolicacid), poly(phosphazenes), L-co-G, other bioabsorbable polymer such as Dacron or other known surgical plastics, a natural biologically derived material such as collagen, a ceramic (with bone-growth enhancers, e.g., hydroxyapatite), PEEK (polyether-etherketone), dessicated biodegradable material, metal, composite materials, a biocompatible textile (e.g., cotton, silk, linen), or other. In one embodiment, the containment device is formed as a long bag-like device and may be used with minimally invasive techniques.

The polymer mesh is generally designed for effective cellular in-growth and complete resorption within three to six months, while not interfering with bone regeneration. The polymer mesh provides a controlled environment for proximate interaction of the implantable composition eliminating issues with graft site migration or irrigation that is often seen with currently available bone graft substitutes. The implant composition of this application can be firmly placed into an appropriate size defect site to maintain volume and provide support for adjacent tissues. Such placement can be accomplished through the use of a variety of devices such as, for example, spatula, forceps, syringe, tamping device or delivered within a polymer mesh.

The implant composition of this application can be tailored to be utilized for a variety of orthopaedic, neurosurgical, and oral and maxillofacial surgical indications in which it would be advantageous to be able to firmly place the composition into a bone defect site such as the repair of simple and compound fractures and nonunions, external fixations, joint reconstructions such as arthrodesis, general arthroplasty, acetabular repair, cup arthroplasty of the hip, femoral and humeral head replacement, femoral head surface replacement and total joint replacements, repairs of the vertebral column including spinal fusion and internal fixation, tumor surgery, for example, deficit filling, discectomy, laminectomy, excision of spinal cord tumors, anterior cervical and thoracic operations, repair of spinal injuries, scoliosis, lordosis and kyphosis treatments, intermaxillary fixation of fractures, mentoplasty, temporomandibular joint replacement, alveolar ridge augmentation and reconstruction, inlay bone grafts, implant placement and revision, sinus lifts, furcation defects, periodontal defects, dental defects, ulna defects, metaphyseal defects, tibia plateau defects, wrist defects, ankle defects, and the like.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A method for producing an implantable bone composition having enhanced osteoinductivity comprising the steps of:
(a) providing a bone material in the form of a demineralized bone matrix comprising a plurality of fully demineralized, entangled bone fibers and surface demineralized bone chips;
(b) dehydrating the bone material via critical point drying with a solvent at its critical point to remove moisture content from the demineralized bone matrix to approximately 8% or less to produce a dehydrated bone material having a surface area with a BET value from about 1 $m^2/gm$ to about 5 $m^2/gm$;
(c) disposing the dehydrated bone material within a polymer mesh;
wherein the weight ratio of the fully demineralized bone fibers to the surface demineralized bone chips within the dehydrated bone material is about 1:0.2.

2. A method of claim 1, the critical point solvent comprises carbon dioxide or freon.

3. A method of claim 2, wherein the dehydrated bone material comprises a surface area increased from about 3 to about 4 times when compared to a surface area of untreated bone material.

4. A method of claim 2, wherein the critical point drying comprises dehydration with carbon dioxide at about 31.5° C. and about 1200 psi.

5. A method of claim 1, wherein the demineralized bone matrix further comprises an osteoinductive additive selected from the group consisting of bone marrow aspirant, blood, blood products, synthetic and naturally-derived bone morphogenic proteins, growth factors, or mixtures thereof.

6. A method of claim 1, wherein the demineralized bone matrix further comprises an osteoconductive additive selected from the group consisting of calcium phosphates, collagen, collagen-derivatives, calcium sulfate, naturally-derived allogenic bone mineral, naturally-derived autogenic bone mineral or mixtures thereof.

7. A method of claim 1, wherein the plurality of fully demineralized bone fibers are dehydrated bone fibers comprising a surface area increased from about 6 to about 7 times when compared to a surface area of bone fibers of untreated demineralized bone matrix.

8. A method of claim 1, wherein the dehydrated fibers of demineralized bone matrix comprise a surface area increased by about 100 times when compared to demineralized bone matrix fibers dried by vacuum or lyophilized.

9. A method of claim 1, wherein the plurality of fully demineralized bone fibers are dehydrated bone fibers comprising a surface area having a BET value from about 40 $m^2/gm$ to about 100 $m^2/gm$.

10. A method of claim 1, wherein the plurality of fully demineralized bone fibers have an aspect ratio of about 50:1 to about 750:1.

11. A method of claim 1, wherein the residual moisture content of the demineralized bone matrix is approximately 3%.

12. A method of claim 1, wherein the polymer mesh is porous.

13. A method of claim 1, wherein the polymer mesh comprises poly(lactic acid-glycolic acid), poly(lactic acid) or poly(glycolic acid).

* * * * *